(12) United States Patent
Cao et al.

(10) Patent No.: US 11,826,192 B2
(45) Date of Patent: Nov. 28, 2023

(54) RADIATION DETECTION APPARATUS

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 347 days.

(21) Appl. No.: 17/176,632

(22) Filed: Feb. 16, 2021

(65) Prior Publication Data

US 2021/0161499 A1 Jun. 3, 2021

Related U.S. Application Data

(63) Continuation of application No. PCT/CN2018/104599, filed on Sep. 7, 2018.

(51) Int. Cl.
 *G01T 1/24* (2006.01)
 *A61B 6/00* (2006.01)
 *A61B 6/04* (2006.01)

(52) U.S. Cl.
 CPC .......... *A61B 6/5294* (2013.01); *A61B 6/0407* (2013.01); *G01T 1/242* (2013.01)

(58) Field of Classification Search
 CPC ...... A61B 6/5294; A61B 6/0407; G01T 1/242
 See application file for complete search history.

(56) References Cited

U.S. PATENT DOCUMENTS

| 4,618,773 | A | * | 10/1986 | Drukier | G01T 1/2008 |
| | | | | | 250/374 |
| 5,847,398 | A | * | 12/1998 | Shahar | G01T 1/243 |
| | | | | | 250/370.09 |
| 7,297,958 | B2 | | 11/2007 | Kojima et al. | |
| 9,116,249 | B1 | * | 8/2015 | Claus | G01T 1/16 |
| 2003/0108147 | A1 | * | 6/2003 | Kojima | A61B 6/4241 |
| | | | | | 378/19 |
| 2008/0061395 | A1 | | 3/2008 | Tkaczyk et al. | |
| 2010/0204942 | A1 | | 8/2010 | Danielsson et al. | |
| 2016/0113604 | A1 | * | 4/2016 | Noshi | A61B 6/5282 |
| | | | | | 600/431 |
| 2018/0188392 | A1 | * | 7/2018 | Polf | A61N 5/1049 |
| 2018/0252825 | A1 | * | 9/2018 | Benlloch Baviera | |
| | | | | | G01T 1/2002 |
| 2018/0275289 | A1 | * | 9/2018 | Jacobs | G01T 1/1611 |

FOREIGN PATENT DOCUMENTS

| CN | 206649168 U | 11/2017 |
| CN | 107613871 A | 1/2018 |
| CN | 108271415 A | 7/2018 |
| GB | 1463451 A | 2/1977 |
| TW | 201816424 A | 5/2018 |

* cited by examiner

*Primary Examiner* — Hugh Maupin
(74) *Attorney, Agent, or Firm* — IPRO, PLLC; Qian Gu

(57) ABSTRACT

Disclosed herein is an apparatus, comprising: a platform configured to support a human body on a first surface of the platform; a first set of radiation detectors arranged in a first layer, wherein the radiation detectors of the first set are attached to a second surface of the platform opposite the first surface; wherein the radiation detectors of the first set are configured to detect radiation from a radiation source inside the human body.

25 Claims, 9 Drawing Sheets

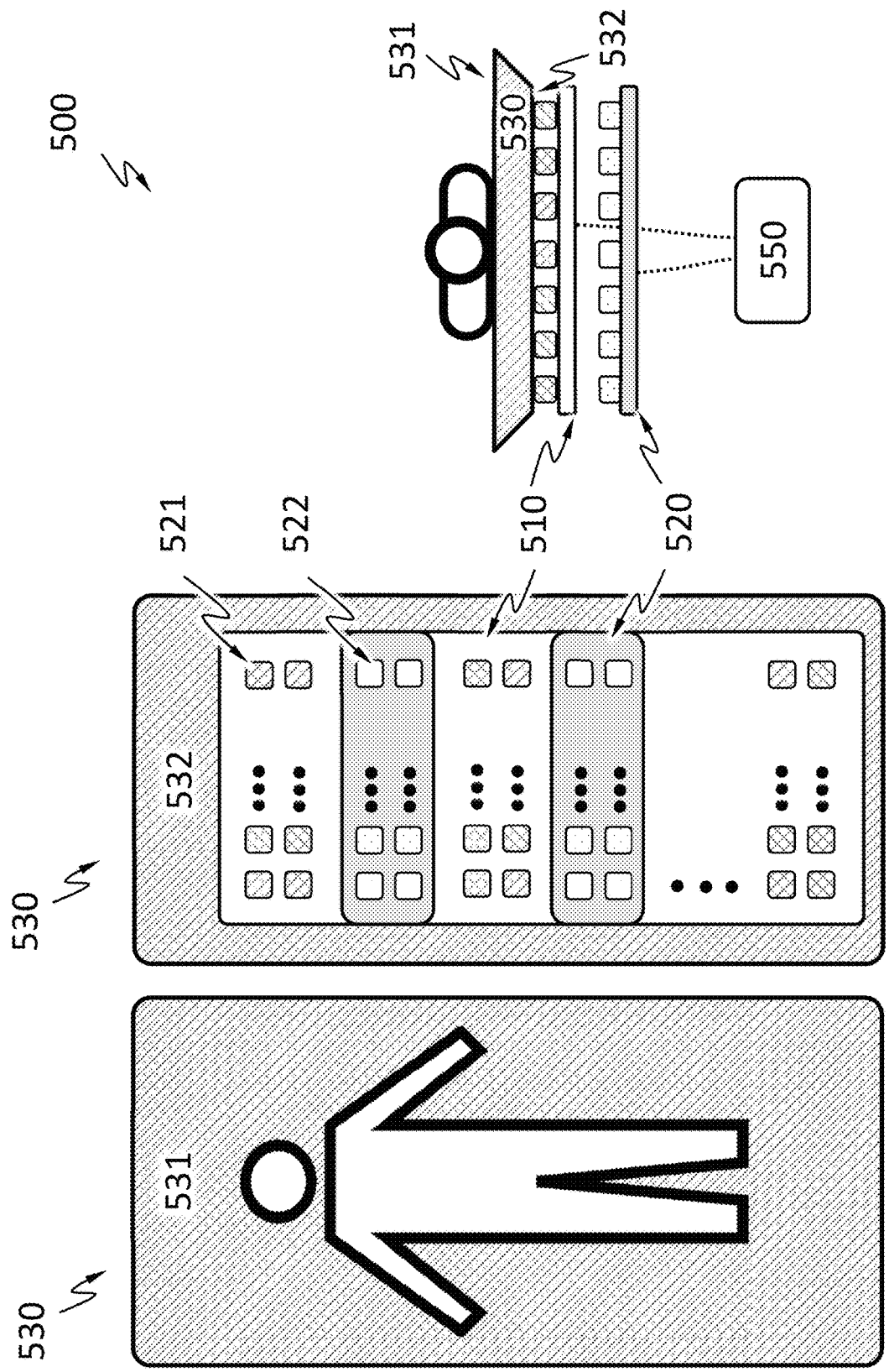

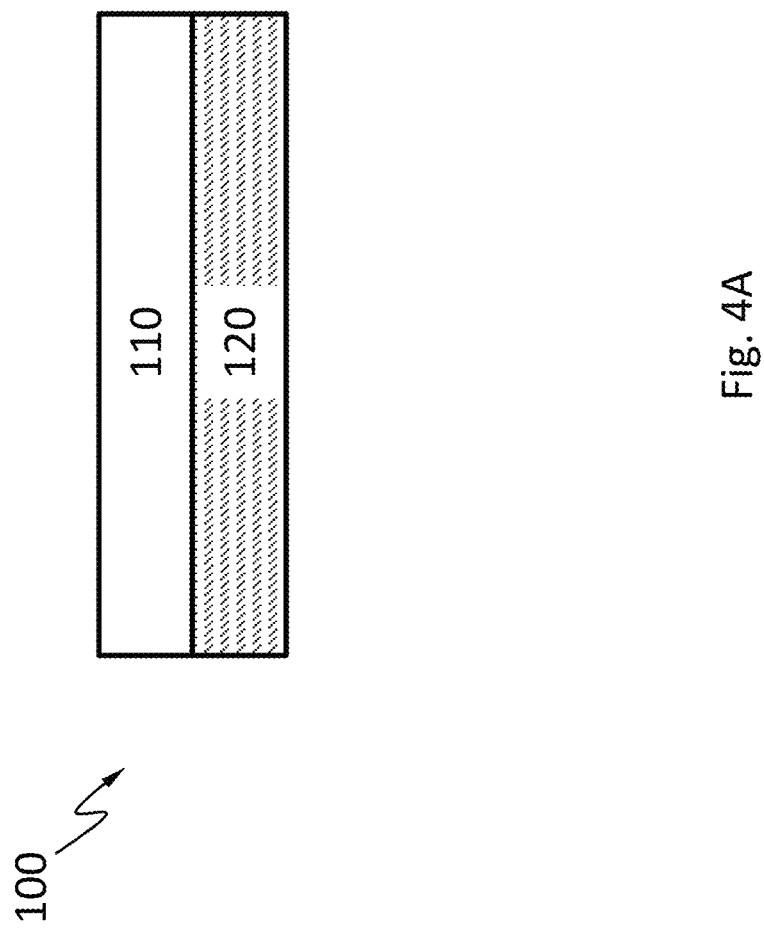

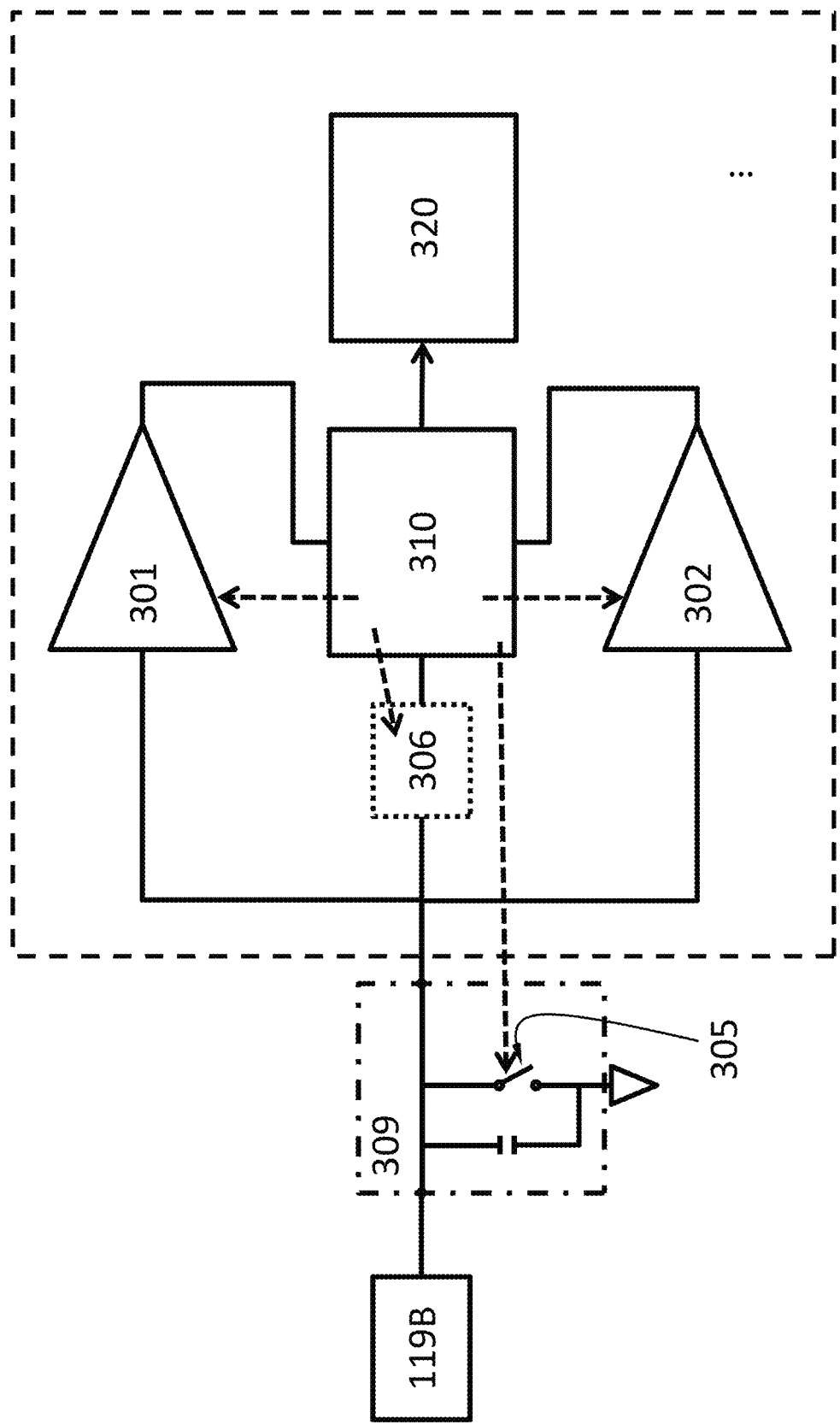

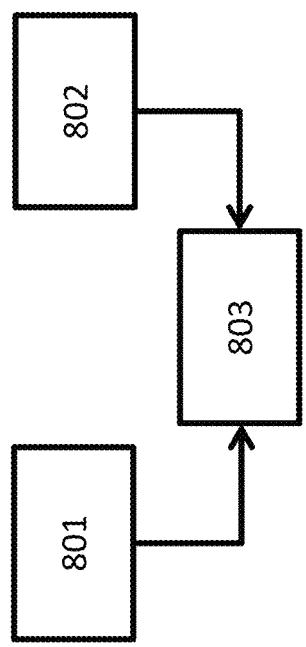

RADIATION DETECTION APPARATUS

BACKGROUND

Radiation detectors may be devices used to measure the flux, spatial distribution, spectrum or other properties of radiations. Radiation detectors may be used for many applications. One important application is imaging. Radiation imaging is a radiography technique and can be used to reveal the internal structure of a non-uniformly composed and opaque object such as the human body.

Early radiation detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to radiation, electrons excited by radiation are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of radiation detectors are radiation image intensifiers. Components of a radiation image intensifier are usually sealed in a vacuum. In contrast to photographic plates, photographic films, and PSP plates, radiation image intensifiers may produce real-time images, i.e., do not require post-exposure processing to produce images. radiation first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident radiation. The emitted electrons are projected, through electron optics, onto an output phosphor and cause the output phosphor to produce a visible-light image.

Scintillators operate somewhat similarly to radiation image intensifiers in that scintillators (e.g., sodium iodide) absorb radiation and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of radiation. A scintillator thus has to strike a compromise between absorption efficiency and resolution.

Semiconductor radiation detectors largely overcome this problem by direct conversion of radiation into electric signals. A semiconductor radiation detector may include a semiconductor layer that absorbs radiation in wavelengths of interest. When a particle of radiation is absorbed in the semiconductor layer, multiple charge carriers (e.g., electrons and holes) are generated and swept under an electric field towards electric contacts on the semiconductor layer.

SUMMARY

Disclosed herein is an apparatus, comprising: a platform configured to support a human body on a first surface of the platform; a first set of radiation detectors arranged in a first layer, wherein the radiation detectors of the first set are attached to a second surface of the platform opposite the first surface; wherein the radiation detectors of the first set are configured to detect radiation from a radiation source inside the human body.

According to an embodiment, each of the radiation detectors of the first set is configured to detect an image of the radiation.

According to an embodiment, the first set of radiation detectors comprises two members, an area of the first layer between which is devoid of any radiation detector.

According to an embodiment, the radiation is beta rays or gamma rays.

According to an embodiment, at least one radiation detector of the radiation detectors of the first set comprises a first radiation absorption layer configured to absorb the radiation and generate electrical signals from the radiation.

According to an embodiment, the first radiation absorption layer comprises silicon or GaAs.

According to an embodiment, the apparatus further comprises a second set of radiation detectors arranged in a second layer; wherein the radiation detectors of the second set are farther away from the second surface of the platform than the radiation detectors of the first set; wherein the radiation detectors of the second set are configured to detect radiation from the radiation source.

According to an embodiment, each of the radiation detectors of the second set is spaced apart from the second surface of the platform by a same distance.

According to an embodiment, each of the radiation detectors of the second set is configured to detect an image of the radiation.

According to an embodiment, the second set of radiation detectors comprises two members, an area of the second layer between which is devoid of any radiation detector.

According to an embodiment, the radiation detectors of the second set comprise a second radiation absorption layer configured to absorb the radiation and generate electrical signals from the radiation.

According to an embodiment, the second radiation absorption layer comprises silicon or GaAs.

According to an embodiment, the apparatus further comprises a processor configured to determine a spatial distribution of the radiation source in the human body based on the radiation detected by the first set of radiation detectors.

According to an embodiment, the first radiation absorption layer comprises an electric contact.

According to an embodiment, the at least one radiation detector comprises: a first voltage comparator configured to compare a voltage of the electric contact to a first threshold; a second voltage comparator configured to compare the voltage to a second threshold; a counter configured to register a number of particles of radiation incident on a pixel of the at least one radiation detector; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the at least one of the numbers to increase by one, when the second voltage comparator determines that an absolute value of the voltage equals or exceeds an absolute value of the second threshold.

Disclosed herein is a method comprising: detecting radiation from a radiation source inside a human body using a first set of radiation detectors arranged in a first layer; detecting radiation from the radiation source using a second set of radiation detectors arranged in a second layer; determining a spatial distribution of the radiation source based on the radiation detected using the first set of radiation detectors and the radiation detected using the second set of radiation detectors; wherein the first layer and the second layer are at different distances from the human body.

According to an embodiment, the method of detecting the radiation from the radiation source using the first set of radiation detectors comprises detecting an image of the radiation.

According to an embodiment, the first set of radiation detectors comprises two members, an area of the first layer between which is devoid of any radiation detectors.

According to an embodiment, the radiation detectors of the first set comprise a first radiation absorption layer configured to absorb the radiation and generate electrical signals from the radiation.

According to an embodiment, the first radiation absorption layer comprises silicon or GaAs.

According to an embodiment, the method of detecting the radiation from the radiation source using the second set of radiation detectors comprises detecting an image of the radiation.

According to an embodiment, each of the radiation detectors of the second set is spaced apart from the second surface of the platform by a same distance.

According to an embodiment, the second set of radiation detectors comprises two members, an area of the second layer between which is devoid of any radiation detectors.

According to an embodiment, the radiation detectors of the second set comprise a radiation absorption layer configured to absorb the radiation and generate electrical signals from the radiation.

According to an embodiment, the radiation absorption layer comprises silicon or GaAs.

According to an embodiment, the radiation is beta rays or gamma rays.

BRIEF DESCRIPTION OF FIGURES

FIG. 1A, FIG. 1B, and FIG. 2 each schematically show a view of an apparatus, according to an embodiment.

FIG. 4A shows a cross-sectional schematic of the radiation detector, according to an embodiment.

FIG. 5A and FIG. 5B each show a component diagram of an electronic system of the radiation detector, according to an embodiment.

FIG. 7 schematically shows a flowchart for a method, according to an embodiment.

DETAILED DESCRIPTION

Figure 3:
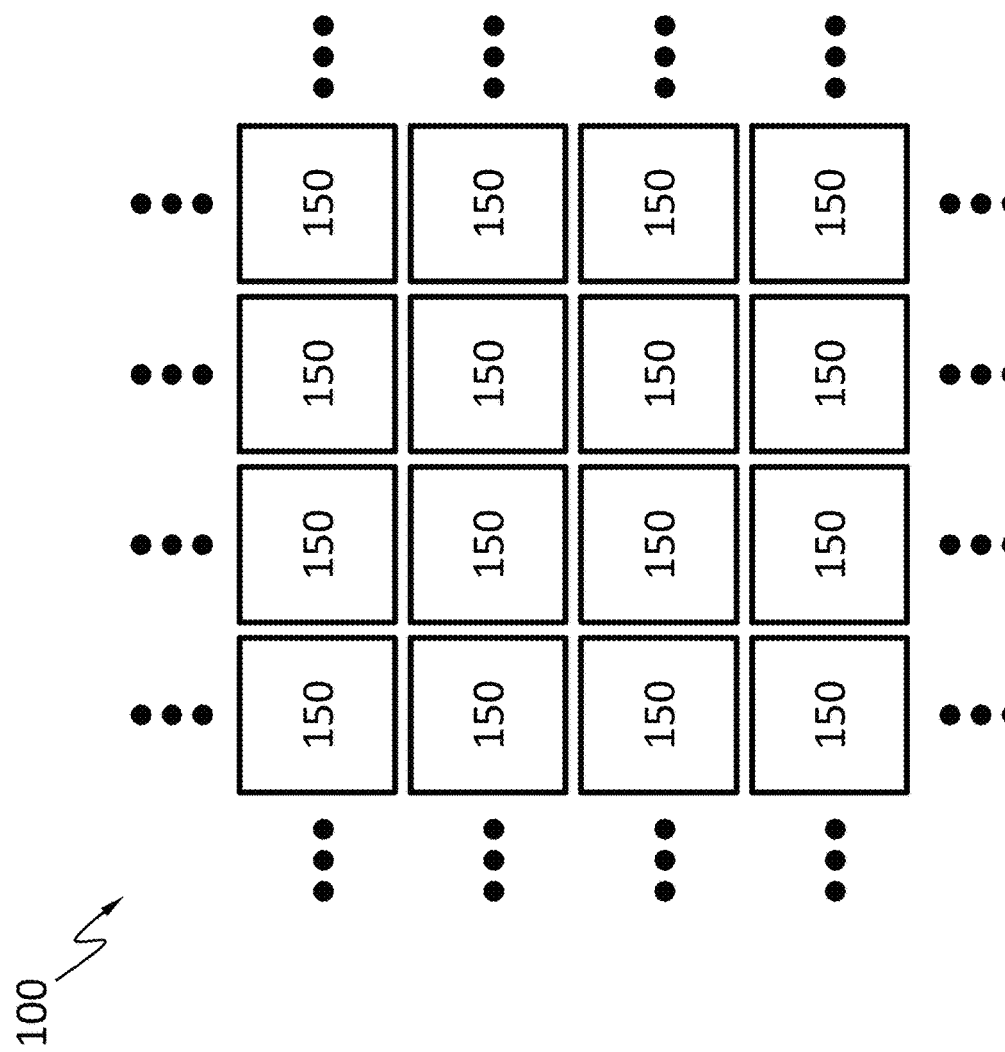
FIG. 3 schematically shows that the apparatus has a radiation detector with an array of pixels, according to an embodiment.

FIG. 1A, FIG. 1B and FIG. 2 each schematically show an apparatus 500 from a different view. FIG. 1A shows a first surface 531 of a platform 530 of the apparatus 500. The first surface 531 of the platform 530 may support a human body. FIG. 1B schematically shows a second surface 532 of the platform 530. The second surface 532 is opposite the first surface 531. The apparatus 500 has a first set of radiation detectors 521 arranged in a first layer 510, as shown in FIG. 1B and FIG. 2. The first set of radiation detectors 521 are attached to the second surface 532. The first set of radiation detectors 521 may include at least two radiation detectors 521. The areas of the first layer 510 between the radiation detectors 521 may be devoid of any radiation detector.

As schematically shown in the FIG. 1B and FIG. 2, the apparatus 500 has a second set of radiation detectors 522 arranged in a second layer 520, according to an embodiment. The second set of radiation detectors 522 are farther away from the second surface 532 than the first set of radiation detectors 521. Each of the second set of radiation detectors 522 may be spaced apart from the second surface 532 by the same distance. Namely, the second layer 520 may be parallel to the second surface 532. The second set of radiation detectors 522 may comprise at least two radiation detectors 522. The areas of the second layer 520 between the radiation detectors 522 may be devoid of any radiation detector. The platform 530 is between the human body and the radiation detectors 521 and 522. The radiation detectors 521 and 522 may detect radiation from a radiation source inside the human body. The radiation detectors 521 and 522 may detect images of the radiation. The radiation may be beta rays or gamma rays.

As shown in FIG. 2, the first layer 510 and the second layer 520 are stacked. The second set of radiation detectors 521 in the second layer 520 may be aligned with the areas of the first layer 510 that are devoid of any radiation detectors.

The radiation source inside the human body may be a radioactive substance introduced into the human body for medical purposes. Examples of the radioactive substance may include iodine-131 ($^{131}$I), iodine-123 ($^{123}$I), and iodine-125 ($^{125}$I). In an example, $^{131}$I is used for treating thyrotoxicosis (hyperthyroidism) and some types of thyroid cancer because the thyroid can absorb iodine. In an example, $^{131}$I is used as a radioactive label for certain radiopharmaceuticals (e.g., $^{131}$I-metaiodobenzylguanidine (131I-MIBG) for imaging and treating pheochromocytoma and neuroblastoma). Knowing the spatial distribution of the radioactive substance thus may facilitate using the radioactive substance for diagnosing or treating certain diseases. The apparatus 500 may have a processor 550 that can determine the spatial distribution of the radiation source based on the radiation detected by the first set of radiation detectors 521 or the second set of radiation detectors 522.

FIG. 3 schematically shows that a radiation detector 100, which is one among the radiation detectors 521 and 522, may have an array of pixels 150, according to an embodiment. The array of the pixels 150 may be a rectangular array, a honeycomb array, a hexagonal array or any other suitable array. The radiation detector 100 may count the numbers of particles of radiation incident on the pixels 150, within a period of time. An example of the particles of radiation is gamma ray photons. Each pixel 150 may be configured to measure its dark current, such as before or concurrently with each particle of radiation incident thereon. The pixels 150 may be configured to operate in parallel. For example, the radiation detector 100 may count one particle of radiation incident on one pixel 150 before, after or while the radiation detector 100 counts another particle of radiation incident on another pixel 150. The pixels 150 may be individually addressable.

FIG. 4A shows a cross-sectional schematic of the radiation detector 100, according to an embodiment. The radiation detector 100 may include a radiation absorption layer 110 and an electronics layer 120 (e.g., an ASIC) for processing or analyzing electrical signals incident particles of radiation generate in the radiation absorption layer 110. The radiation detector 100 may or may not include a scintillator. The radiation absorption layer 110 may include a semiconductor material such as single-crystalline silicon. The semiconductor may have a high mass attenuation coefficient for the radiation of interest.

Figure 4B:
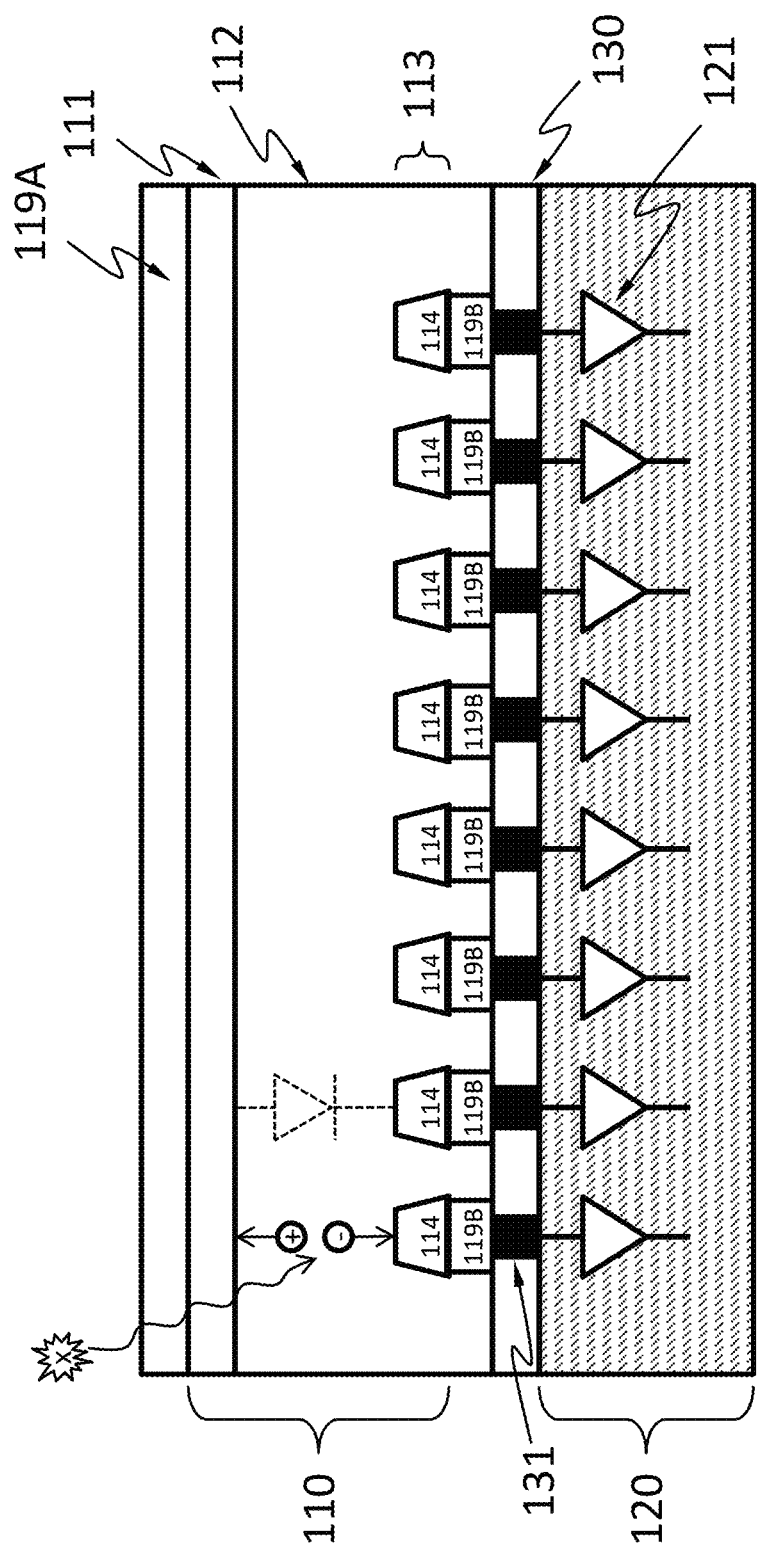
FIG. 4B shows a detailed cross-sectional schematic of the radiation detector, according to an embodiment.

As shown in a more detailed cross-sectional schematic of the radiation detector 100 in FIG. 4B, according to an embodiment, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete regions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 4B, each of the discrete regions 114 of the second doped region 113 forms a diode with the first doped region 111 and the optional intrinsic region 112. Namely, in the example in FIG. 4B, the radiation absorption layer 110 has a plurality of diodes having the first doped region 111 as a shared electrode. The first doped region 111 may also have discrete portions. The radiation absorption layer 110 may have an electric contact 119A in electrical contact with the first doped region 111. The radiation absorption layer 110 may have multiple discrete electric contacts 119B, each of which is in electrical contact with the discrete regions 114.

When particles of radiation hit the radiation absorption layer 110 including diodes, the particles of radiation may be absorbed and generate one or more charge carriers by a number of mechanisms. The charge carriers may drift to the electric contacts 119A and 119B under an electric field. The field may be an external electric field. In an embodiment, the charge carriers may drift in directions such that the charge carriers generated by a single particle of the radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of the radiation incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a particle of the radiation incident therein flow to the discrete region 114. Namely, less than 2%, less than 1%, less than 0.1%, or less than 0.01% of these charge carriers flow beyond the pixel 150.

Figure 4C:
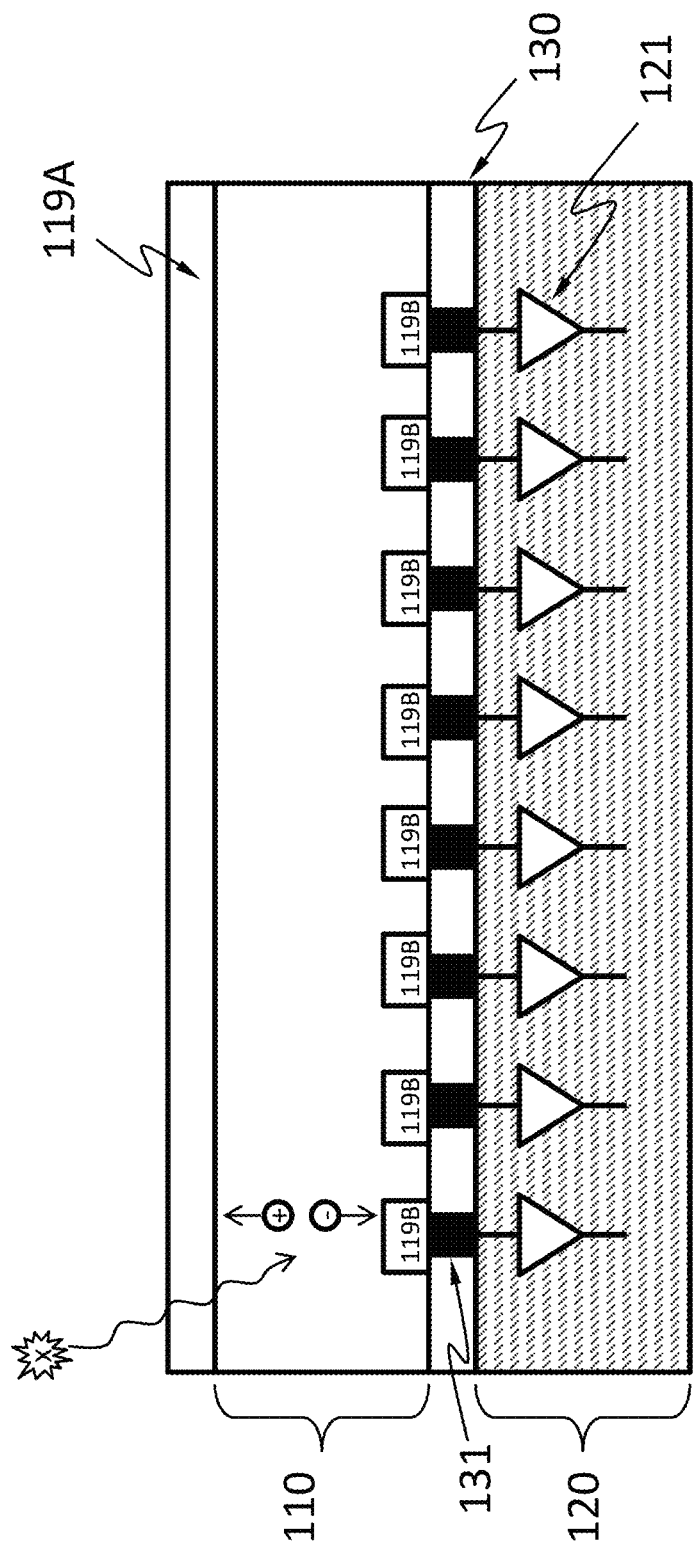
FIG. 4C shows an alternative detailed cross-sectional schematic of the radiation detector, according to an embodiment.

As shown in an alternative detailed cross-sectional schematic of the radiation detector 100 in FIG. 4C, according to an embodiment, the radiation absorption layer 110 may include a resistor of a semiconductor material such as single-crystalline silicon but does not include a diode. The semiconductor may have a high mass attenuation coefficient for the radiation of interest. The radiation absorption layer 110 may have an electric contact 119A in electrical contact with the semiconductor on one surface of the semiconductor. The radiation absorption layer 110 may have multiple electric contacts 119B on another surface of the semiconductor.

When particles of radiation hit the radiation absorption layer 110 including a resistor but not diodes, the particles of radiation may be absorbed and generate one or more charge carriers by a number of mechanisms. A particle of the radiation may generate 10 to 100000 charge carriers. The charge carriers may drift to the electrical contacts 119A and 119B under an electric field. The field may be an external electric field. In an embodiment, the charge carriers may drift in directions such that the charge carriers generated by a single particle of the radiation are not substantially shared by two electrical contacts 119B ("not substantially shared" here means less than 2%, less than 0.5%, less than 0.1%, or less than 0.01% of these charge carriers flow to a different one of the discrete portions than the rest of the charge carriers). Charge carriers generated by a particle of the radiation incident around the footprint of one of the electrical contacts 119B are not substantially shared with another of the electrical contacts 119B. A pixel 150 associated with one of the electrical contacts 119B may be an area around it in which substantially all (more than 98%, more than 99.5%, more than 99.9% or more than 99.99% of) charge carriers generated by a particle of the radiation incident therein flow to that one electrical contact 119B. Namely, less than 2%, less than 0.5%, less than 0.1%, or less than 0.01% of these charge carriers flow beyond the pixel associated with that one electrical contact 119B.

The electronics layer 120 may include an electronic system 121 suitable for processing or interpreting signals generated by the radiation incident on the radiation absorption layer 110. The electronic system 121 may include an analog circuitry such as a filter network, amplifiers, integrators, and comparators, or a digital circuitry such as a microprocessor, and memory. The electronic system 121 may include one or more ADCs. The electronic system 121 may include components shared by the pixels or components dedicated to a single pixel. For example, the electronic system 121 may include an amplifier dedicated to each pixel 150 and a microprocessor shared among all the pixels 150. The electronic system 121 may be electrically connected to the pixels by vias 131. Space among the vias may be filled with a filler material 130, which may increase the mechanical stability of the connection of the electronics layer 120 to the radiation absorption layer 110. Other bonding techniques are possible to connect the electronic system 121 to the pixels without using vias.

Figure 5A:
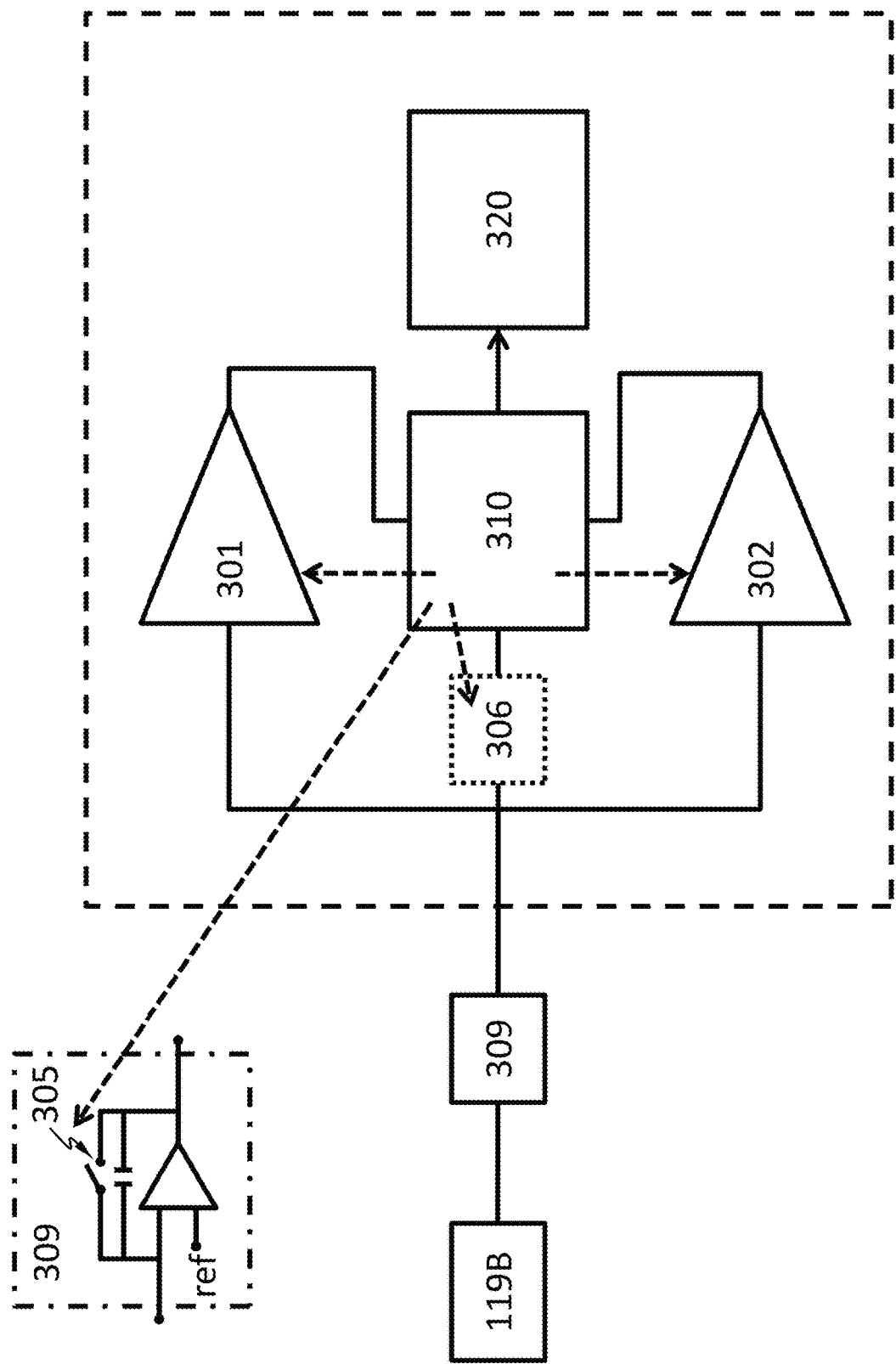

FIG. 5A and FIG. 5B each show a component diagram of the electronic system 121, according to an embodiment. The electronic system 121 may include a first voltage comparator 301, a second voltage comparator 302, a counter 320, a switch 305, an optional voltmeter 306 and a controller 310.

The first voltage comparator 301 is configured to compare the voltage of at least one of the electric contacts 119B to a first threshold. The first voltage comparator 301 may be configured to monitor the voltage directly, or calculate the voltage by integrating an electric current flowing through the electrical contact 119B over a period of time. The first voltage comparator 301 may be controllably activated or deactivated by the controller 310. The first voltage comparator 301 may be a continuous comparator. Namely, the first voltage comparator 301 may be configured to be activated continuously and monitor the voltage continuously. The first voltage comparator 301 may be a clocked comparator. The first threshold may be 5-10%, 10%-20%, 20-30%, 30-40% or 40-50% of the maximum voltage one incident particle of radiation may generate on the electric contact 119B. The maximum voltage may depend on the energy of the incident particle of radiation, the material of the radiation absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, & \text{if } x \geq 0 \\ -x, & \text{if } x \leq 0 \end{cases}.$$

The second threshold may be 200%-300% of the first threshold. The second threshold may be at least 50% of the maximum voltage one incident particle of radiation may generate on the electric contact 119B. For example, the second threshold may be 100 mV, 150 mV, 200 mV, 250 mV or 300 mV. The second voltage comparator 302 and the first voltage comparator 301 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident particles of radiation. However, having a high speed is often at the cost of power consumption.

The counter 320 is configured to register at least a number of particles of radiation incident on the pixel 150 encompassing the electric contact 119B. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold.

The controller 310 may be configured to cause the optional voltmeter 306 to measure the voltage upon expiration of the time delay. The controller 310 may be configured to connect the electric contact 119B to an electrical ground, so as to reset the voltage and discharge any charge carriers accumulated on the electric contact 119B. In an embodiment, the electric contact 119B is connected to an electrical ground after the expiration of the time delay. In an embodiment, the electric contact 119B is connected to an electrical ground for a finite reset time period. The controller 310 may connect the electric contact 119B to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

The electronic system 121 may include an integrator 309 electrically connected to the electric contact 119B, wherein the integrator is configured to collect charge carriers from the electric contact 119B. The integrator 309 can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electric contact 119B accumulate on the capacitor over a period of time ("integration period"). After the integration period has expired, the capacitor voltage is sampled and then reset by a reset switch. The integrator 309 can include a capacitor directly connected to the electric contact 119B.

Figure 6:
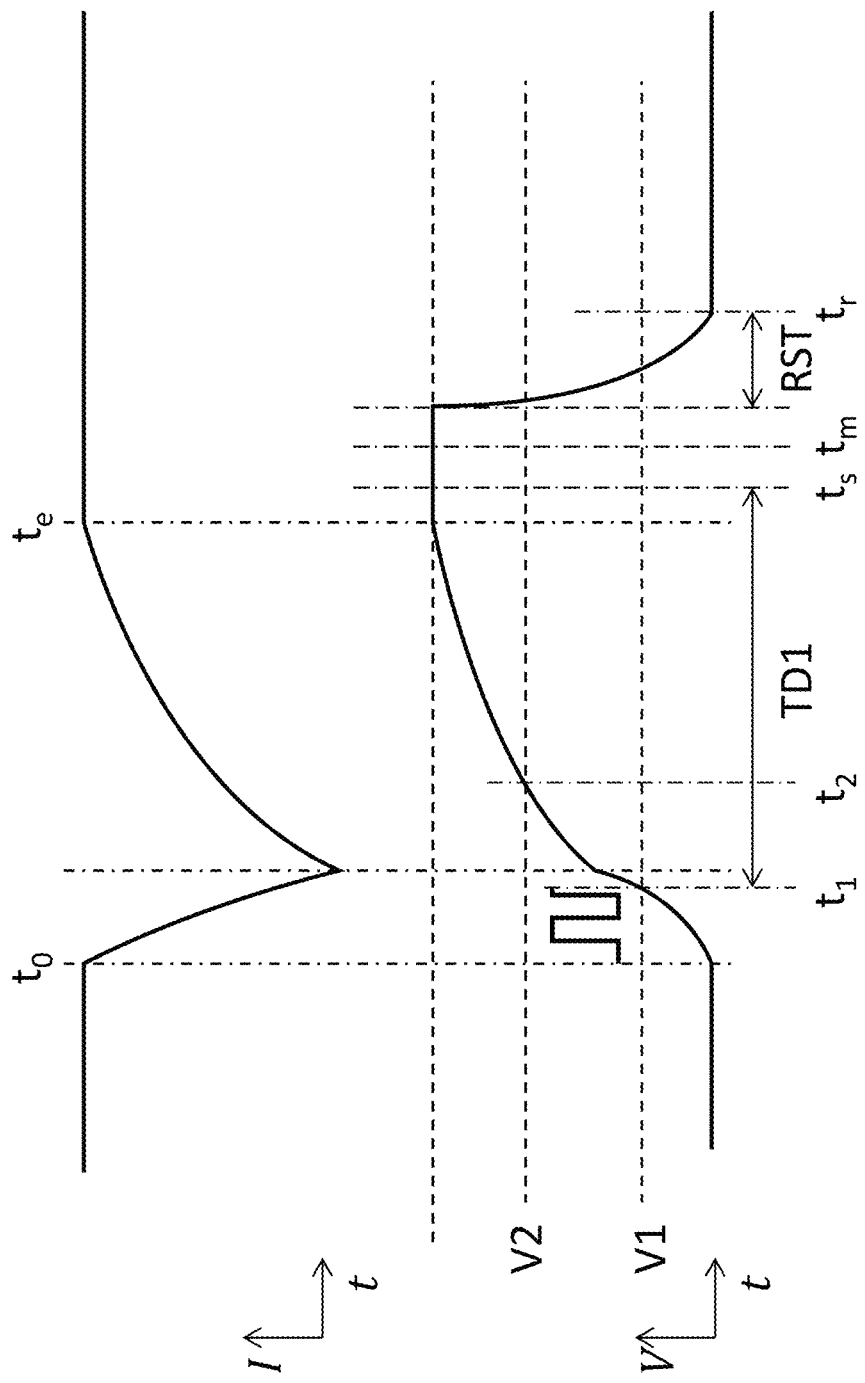
FIG. 6 schematically shows a temporal change of the electric current flowing through an electric contact (upper curve) of the radiation absorption layer of the radiation detector, and a corresponding temporal change of the voltage on the electric contact (lower curve).

FIG. 6 schematically shows a temporal change of the electric current flowing through the electric contact 119B (upper curve) caused by charge carriers generated by a particle of radiation incident on the pixel 150 encompassing the electric contact 119B, and a corresponding temporal change of the voltage of the electric contact 119B (lower curve). The voltage may be an integral of the electric current with respect to time. At time $t_0$, the particle of radiation hits pixel 150, charge carriers start being generated in the pixel 150, electric current starts to flow through the electric contact 119B, and the absolute value of the voltage of the electric contact 119B starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold V2 at time $t_2$, the controller 310 waits for stabilization of the voltage to stabilize. The voltage stabilizes at time $t_e$, when all charge carriers generated by the particle of radiation drift out of the radiation absorption layer 110. At time $t_s$, the time delay TD1 expires. At or after time $t_e$, the controller 310 causes the voltmeter 306 to digitize the voltage and determines which bin the energy of the particle of radiation falls in. The controller 310 then causes the number registered by the counter 320 corresponding to the bin to increase by one. In the example of FIG. 6, time $t_s$ is after time $t_e$; namely TD1 expires after all charge carriers generated by the particle of radiation drift out of the radiation absorption layer 110. If time $t_e$ cannot be easily measured, TD1 can be empirically chosen to allow sufficient time to collect essentially all charge carriers generated by a particle of radiation but not too long to risk have another incident particle of radiation. Namely, TD1 can be empirically chosen so that time $t_s$ is empirically after time $t_e$. Time $t_s$ is not necessarily after time $t_e$ because the controller 310 may disregard TD1 once V2 is reached and wait for time $t_e$. The rate of change of the difference between the voltage and the contribution to the voltage by the dark current is thus substantially zero at $t_e$. The controller 310 may be configured to deactivate the second voltage comparator 302 at expiration of TD1 or at $t_2$, or any time in between.

The voltage at time $t_e$ is proportional to the amount of charge carriers generated by the particle of radiation, which relates to the energy of the particle of radiation. The controller 310 may be configured to determine the energy of the particle of radiation, using the voltmeter 306.

After TD1 expires or digitization by the voltmeter 306, whichever later, the controller 310 connects the electric contact 119B to an electric ground for a reset period RST to allow charge carriers accumulated on the electric contact 119B to flow to the ground and reset the voltage. After RST, the system 121 is ready to detect another incident particle of radiation. If the first voltage comparator 301 has been deactivated, the controller 310 can activate it at any time before RST expires. If the controller 310 has been deactivated, it may be activated before RST expires.

FIG. 7 schematically shows a flowchart for a method, according to an embodiment. In procedure 801, a radiation emitted from a radiation source inside a human body is detected by the first set of radiation detectors 521. In procedure 802, the radiation is detected by the second set of radiation detectors 522. In procedure 803, a spatial distribution of the radiation source inside the human body is determined, based on the radiation detected by the first set of radiation detectors 521 and the radiation detected by the second set of radiation detectors 521.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. An apparatus comprising:
   a platform configured to support a human body on a first surface of the platform;
   a first set of radiation detectors arranged in a first layer, wherein the radiation detectors of the first set are attached to a second surface of the platform opposite the first surface;
   wherein the radiation detectors of the first set are configured to detect radiation from a radiation source inside the human body.
2. The apparatus of claim 1, wherein each of the radiation detectors of the first set is configured to detect an image of the radiation.
3. The apparatus of claim 1, wherein the first set of radiation detectors comprises two members, an area of the first layer between which is devoid of any radiation detector.
4. The apparatus of claim 1, wherein the radiation is beta rays or gamma rays.
5. The apparatus of claim 1, wherein at least one radiation detector of the radiation detectors of the first set comprises a first radiation absorption layer configured to absorb the radiation and generate electrical signals from the radiation.
6. The apparatus of claim 5, wherein the first radiation absorption layer comprises silicon or GaAs.
7. The apparatus of claim 1, further comprising a second set of radiation detectors arranged in a second layer;
   wherein the radiation detectors of the second set are farther away from the second surface of the platform than the radiation detectors of the first set;
   wherein the radiation detectors of the second set are configured to detect radiation from the radiation source.
8. The apparatus of claim 7, wherein each of the radiation detectors of the second set is spaced apart from the second surface of the platform by a same distance.
9. The apparatus of claim 7, wherein each of the radiation detectors of the second set is configured to detect an image of the radiation.
10. The apparatus of claim 7, wherein the second set of radiation detectors comprises two members, an area of the second layer between which is devoid of any radiation detector.
11. The apparatus of claim 7, wherein the radiation detectors of the second set comprise a second radiation absorption layer configured to absorb the radiation and generate electrical signals from the radiation.
12. The apparatus of claim 11, wherein the second radiation absorption layer comprises silicon or GaAs.

13. The apparatus of claim 1, further comprising a processor configured to determine a spatial distribution of the radiation source in the human body based on the radiation detected by the first set of radiation detectors.

14. The apparatus of claim 5, wherein the first radiation absorption layer comprises an electric contact.

15. The apparatus of claim 14, wherein the at least one radiation detector comprises:
a first voltage comparator configured to compare a voltage of the electric contact to a first threshold;
a second voltage comparator configured to compare the voltage to a second threshold;
a counter configured to register a number of particles of radiation incident on a pixel of the at least one radiation detector;
a controller;
wherein the controller is configured to start a time delay from a time at which the first voltage comparator determines that an absolute value of the voltage equals or exceeds an absolute value of the first threshold;
wherein the controller is configured to activate the second voltage comparator during the time delay;
wherein the controller is configured to cause the number to increase by one, when the second voltage comparator determines that an absolute value of the voltage equals or exceeds an absolute value of the second threshold.

16. A method comprising:
detecting radiation from a radiation source inside a human body using a first set of radiation detectors arranged in a first layer;
detecting radiation from the radiation source using a second set of radiation detectors arranged in a second layer;
determining a spatial distribution of the radiation source based on the radiation detected using the first set of radiation detectors and the radiation detected using the second set of radiation detectors;
wherein the first layer and the second layer are at different distances from the human body;
wherein the first set of radiation detectors comprises two members, an area of the first layer between which is devoid of any radiation detector;
wherein the second set of radiation detectors are aligned with the area.

17. The method of claim 16, wherein detecting the radiation from the radiation source using the first set of radiation detectors comprises detecting an image of the radiation.

18. The method of claim 16, wherein the radiation detectors of the first set comprise a first radiation absorption layer configured to absorb the radiation and generate electrical signals from the radiation.

19. The method of claim 18, wherein the first radiation absorption layer comprises silicon or GaAs.

20. The method of claim 16, wherein detecting the radiation from the radiation source using the second set of radiation detectors comprises detecting an image of the radiation.

21. The method of claim 16, wherein each of the radiation detectors of the second set is spaced apart from the first layer by a same distance.

22. The method of claim 16, wherein the second set of radiation detectors comprises two members, an area of the second layer between which is devoid of any radiation detectors.

23. The method of claim 16, wherein the radiation detectors of the second set comprise a radiation absorption layer configured to absorb the radiation and generate electrical signals from the radiation.

24. The method of claim 23, wherein the radiation absorption layer comprises silicon or GaAs.

25. The method of claim 16, wherein the radiation is beta rays or gamma rays.

* * * * *